United States Patent [19]

Schlossman et al.

[11] Patent Number: 5,002,869
[45] Date of Patent: Mar. 26, 1991

[54] MONOCLONAL ANTIBODY SPECIFIC TO A NOVEL EPITOPE OF THE LFA-1 ANTIGEN OF HUMAN T LYMPHOCYTES

[75] Inventors: Stuart F. Schlossman, Newton Center; Chikao Morimoto, Needham, both of Mass.

[73] Assignee: Dana-Farber Cancer Institute, Boston, Mass.

[21] Appl. No.: 116,514

[22] Filed: Nov. 2, 1987

[51] Int. Cl.$^5$ ............... A61K 39/395; G01N 33/567; G01N 33/577; C12N 15/00
[52] U.S. Cl. ............................... 435/7.24; 424/1.1; 424/85.91; 424/34; 424/172.2; 424/240.27; 424/948; 436/503; 436/548; 530/387; 530/391; 530/809; 935/104; 935/110
[58] Field of Search ............... 435/7, 34, 172, 2, 240, 435/27, 948; 424/85.8, 85.91; 436/503, 548; 530/387, 391, 808, 809; 935/102, 104, 107, 110

[56] References Cited

U.S. PATENT DOCUMENTS

| | | | |
|---|---|---|---|
| 4,443,427 | 4/1984 | Reinherz et al. | 424/85.91 |
| 4,550,086 | 10/1985 | Reinherz et al. | 436/506 |
| 4,677,056 | 6/1987 | Dupont et al. | 435/7 |

FOREIGN PATENT DOCUMENTS 0235805  9/1987  European Pat. Off. .

OTHER PUBLICATIONS

Bai et al., *Eur. Journ. Immunol.*, 13, 521–527, 1983.
LeBien et al., *Journ. Immunol.*, 125, 2208–2214, 1980.
Al—Sakkaf et al., *Biol. Abstr.*, 81, Abstr. No. 62873, 1986.
Hall, *Molecular Immunology*, 22, 757–764, 1985.
Sanchez-Madrid et al., *Proc. Natl. Acad. Sci. U.S.A.*, 79, 7489–7493, 1982.
Spits et al., *Hybridoma*, 2, 423–437, 1983.
Springer et al., *Ann. Rev. Immunol.*, 5, 223–252, 1987.
Todd et al., In Reinherz (ED), Leukocyte Typing (PAP. Int. Workshop), 2nd 1984 (Pub 1986), 3 pp. 95–108, Springer Publishers, New York.

*Primary Examiner*—Esther L. Kepplinger
*Assistant Examiner*—David A. Saunders
*Attorney, Agent, or Firm*—Myron C. Cass

[57] ABSTRACT

A monoclonal antibody which binds preferentially to a subset of the human CD8 lymphocyte population whereby to positively and precisely distinguish between cytotoxic effector and supressor effector cells in the CD8 cell population. The monoclonal antibody recognizes a novel epitope of LFA-1 antigen by means of which it can bind CD8 cells which express the eptope on a surface antigen thereof. The CD8 subset cell population to which this anitbody binds preferentially is the CD8 cytotoxic effector population. This selectivity of the monoclonal antibody enables cell sorting, diagnostic and positive therapeutic applications thereof to be utilized.

22 Claims, 3 Drawing Sheets

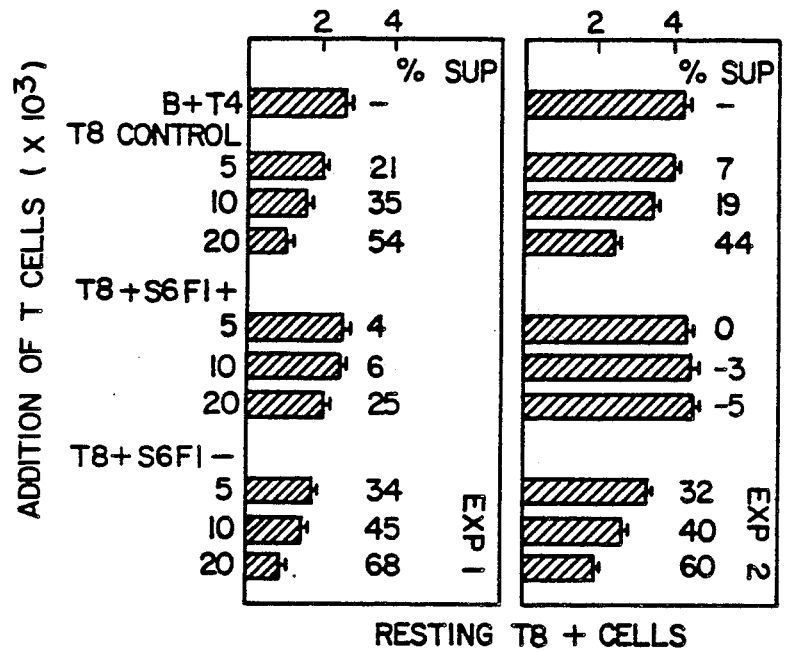
FIG. 3A  PWM-STIMULATED IgG SECRETION ($1 \times 10^3$ ng/ml)
RESTING T8+ CELLS
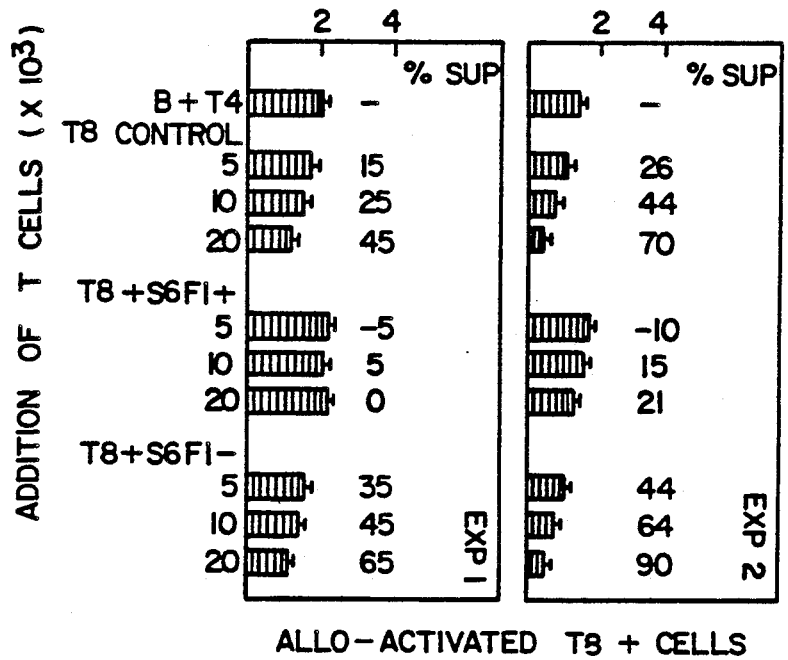
FIG. 3B  ALLO-STIMULATED IgG SECRETION ($1 \times 10^3$ ng/ml)
ALLO-ACTIVATED T8+ CELLS

MONOCLONAL ANTIBODY SPECIFIC TO A NOVEL EPITOPE OF THE LFA-1 ANTIGEN OF HUMAN T LYMPHOCYTES

This invention was made with Government support in part by National Institutes of Health grants AI12069 25369 and AM33713. The government has rights in the invention.

This invention relates to monoclonal antibodies and more particularly, relates to a monoclonal antibody which is specific to a novel epitope on the lymphocyte function associate antigen (LFA-1) which enables distinguishing between killer effector and suppressor effector cells in human T8 lymphocyte populations.

BACKGROUND OF THE INVENTION

Developments in hybridoma technology have contributed to a better understanding of the manner in which the human immune response system functions. Antigens introduced into the human body stimulate the immune response system whereby lymphocyte cells synthesize antibody molecules capable of binding to determinants on the antigens. A cocktail of antibodies is produced in the antisera which is complex, variable in composition and capable of different effects when administered to different recipients. Hybridoma technology has enabled production of hybrid cell lines capable of reproducing monoclonal antibodies of predefined specificity (Kohler and Milstein, Nature 256, 495–597, 1975). The monoclonal antibodies produced by this technology have been utilized to study T and B lymphocyte functions in the regulation of the immune response in humans. In this study, a better recognition of the functions of human T lymphocyte sub-populations has been derived.

Human T lymphocytes are capable of recognizing specific antigens, execute inducer and suppressor functions and regulate the type and intensity of virtually all cellular and humoral immune responses. Two human major T cell subsets with unique regulatory and effector functions were identified as T4 and T8 subsets on the basis of the individual cell surface glycoproteins that they express. The T4 subset was shown to provide inducer/helper functions and the T8 subset to function in a suppressive mode. Also, monoclonal antibodies were developed which are capable of dividing T cells into functionally distinct T4 and T8 populations which also show preferential recognition of different classes of antigens respectively. Morimoto et al., J. Immunol., 134: 1508–1515 (1985).

Studies with monoclonal antibodies have shown that the T4 cells recognize Class II antigens of the major histocompatibility complex (MHC) while T8 cells recognize Class I MHC antigens. Meuer et al., Proc. Natl. Acad. Sci. U.S.A., 79:4395–4399 (1982). It has been determined that considerable functional as well as phenotypic heterogeneity exists within the T4 and T8 cell subsets. Although the T8+ (CD8+) population contains precytotoxic, pre-suppressor and suppressor effector T cells, these distinctions still rest in large measure on the use of functional assays. Clement et al., J. Immunol, 133:2461–2468 (1984) relates attempts to define the CD8+ precursor of the killer cells of the immune system using monoclonal antibodies. Previous attempts to provide a positive and usefully precise phenotyping means, i.e., a monoclonal antibody, to distinguish between cytotoxic effector and suppressor effector cells within the CD8 class of cells have not been successful or the distinctions could not be made readily. Takeuchi et al., Cellular Immunol, (in press) shows that the CD8+CD11 (T8+ —) subset contains both suppressor and cytotoxic effector cells whereas the T8+Mo1+ subset contained NK cells. Thus, suppression seen in the T8+Mo1— subset has the characteristics of the conventional suppressor system in that it requires an inducer of suppression, namely, T4+2H4+. The T8+Mo1+ (CD11) subset of cells which suppresses does not require a suppressor inducer cell, but rather functions as an NK cell. Thus, Takeuchi et al. shows that the T8+CD11— subset contained both suppressor and effector cells. This study showed that there is no monoclonal antibody which can be used to precisely divide the CD8+CD11— subset into suppressor effector cells and cytotoxic effector cells.

In the study of cytolytic T lymphocyte mediated killing, the lymphocyte function associated antigen (LFA-1) was found to be important. Sanchez-Madrid et al., J. Exp. Med., 158:1758–1803 (1983). Human LFA-1 is a high molecular weight surface antigen containing alpha ($\alpha$) and beta ($\beta$) polypeptide chains non-covalently associated. The alpha unit was determined to have a molecular weight of 177,000 daltons and the beta unit to have a molecular weight of 95,000 daltons.

The LFA-1 is a molecule which functions to strengthen adhesions between effector cells and target cells. It was found to act together with the antigen receptor in human cytotoxic T lymphocytes (CTL) mediated killing. The LFA-1 molecule is present on both B and T lymphocytes and marks sub-populations that differ in quantitative expression. Monoclonal antibodies have been developed to recognize three distinct antigens associated with human T lymphocyte mediated cytolysis, thereby suggesting the complexity of understanding the process involving antigen recognition and adhesion of the cytolytic T lymphocyte (CTL) to the target cell, and lysing of the cell targeted. These antigens were identified as LFA-1, LFA-2 and LFA-3. Sanchez-Madrid et al., Proc. Natl. Acad. Sci. U.S.A., 79:7489–7493 (1982). See also Hildreth et al., Eur. J. Immunol., 13:202–208 (1982) for a discussion relating to involvement of human LFA-1 in cell mediated lympholysis. It is clear that more precise phenotypic distinction is desirable between the functional populations within the CD8+ cells.

Although the general scheme of hybridoma and monoclonal antibody production is well known at this stage of implementation, great care must be exercised in the separation and maintenance of hybridoma cells in culture. Isolated clones have been known to produce antibodies against a subject antigen which differs from clone to clone since antibodies produced by different cells may react with different antigenic determinants on the same molecule. Adequate testing of the resulting antibody or antibody-containing medium, serum or ascitic fluid is essential. It is necessary to characterize the antibody of each clone which contributes to the complexity of producing monoclonal antibodies which are to be utilized in both diagnostic and therapeutic applications.

In developing a desired monoclonal antibody, one must identify and locate the antigenic determinant which will elicit a specific antibody to bind with it. Or, conversely, develop several hundred hybridoma clones from fusions performed and exhaustively screen them against normal and nonnormal tissue and different antigens in identifying and defining that clone which produces the antibody with desired binding specificity. The object of this invention is to produce a monoclonal antibody which binds to a particular antigenic determinant expressed on the surface of human T8 (CD8) cells which enables such functional populations within this T cell population to be determined. A monoclonal antibody is provided which enables a more precise phenotyping of the CD8 class of cells so as to distinguish between cytotoxic effector and suppressor effector cells within that cell class.

SUMMARY OF THE INVENTION

A monoclonal antibody is developed which can distinguish killer effector and suppressor effector cells in a CD8 lymphocyte population. The surface antigen or determinant for which the monoclonal antibody is specific is comprised of an 180,000 dalton and 95,000 dalton glycoprotein. The antigen is designated "S6F1" and the monoclonal antibody appears to recognize a novel epitope on the LFA-1 antigen.

The S6F1 antigen is expressed preferentially on the T8+ sub-population of lymphocytes, but was recognized by the monoclonal antibody in a study of unfractionated T cells and T4+ lymphocytes in very small degrees. This specificity for the S6F1 antigen enabled the monoclonal antibody to be used to sub-divide the T8+ population in a human peripheral blood lymphocyte sample so as to assess the functional heterogeneity of these cells. The monoclonal antibody was utilized to define the LFA-1 antigen and its function in the process of cytotoxicity which was previously unknown.

BRIEF DESCRIPTION OF THE DRAWINGS

FIGS. 3A and 3B are graphs developed to show the relationship between suppressor effector activity and T8 cell populations bearing the S6F1 antigen.

DESCRIPTION OF PREFERRED EMBODIMENTS

Monoclonal Antibody Development Balb/C mice were immunized with the cell line 1670 which is an immortalized splenocyte population derived from *Herpesvirus saimiri* infected whitelip tamarin using standard hybridoma procedures. The mouse spleen cells were harvested and fused with P3/NS1/1-AG4-1 myeloma cells in polyethylene glycol. The cell populations were cultured in HAT medium to obtain hybridoma cells to be cloned, assayed for monoclonal antibody production, and monoclonal antibodies produced for screening and specificity selection.

Peripheral blood lymphocytes were separated from blood samples obtained from healthy donors by Ficoll-Hypaque density gradient centrifugation. The lymphocytes were separated into T and non-T cell populations by E rosette formation with sheep erythrocytes as described in Meuer et al., supra. Initially, monoclonal antibodies were screened for reactivity with T cells to discern any pattern of specific cell binding. T4 and T8 lymphocyte cells were obtained by complement-mediated lysis with T4 monoclonal antibody and T8 antibody respectively and then reactivity with monoclonal antibody analyzed by cell sorting prodcedures using an EPICS® instrument marketed by Coulter Corporation of Hialeah, Fla. The monoclonal antibody embodying the invention was determined after analysis for reactivity with unfractionated T, T4 and T8 cells and characterized as reactive preferentially with T8 cells and binding specifically to the antigen identified herein as "S6F1". The monoclonal antibody, anti-S6F1, can distinguish killer effector and suppressor effector cells in T8 lymphocyte populations. The monoclonal antibody defines a cell surface structure comprised of a 180,000 dalton and 95,000 dalton molecular weight glycoprotein. Sequential immunoprecipitation studies and two dimensional gel analysis, as will be fully discussed, indicate that the S6F1 monoclonal antibody recognizes a novel epitope on the LFA-1 antigen.

Figure 1A:
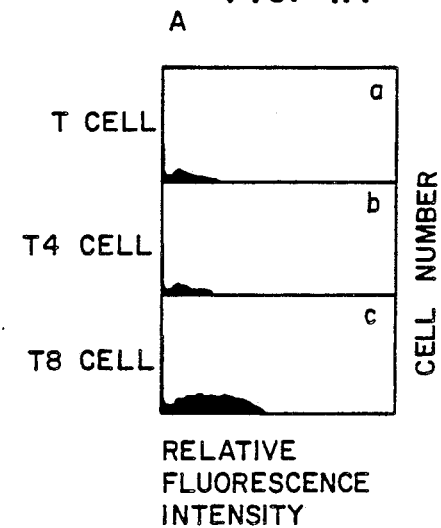
FIGS. 1A and 1B are fluorescence graphs showing the reactivities of the monoclonal antibody embodying the invention and known monoclonal antibody 2F12, with certain T lymphocytes.
Figure 1B:
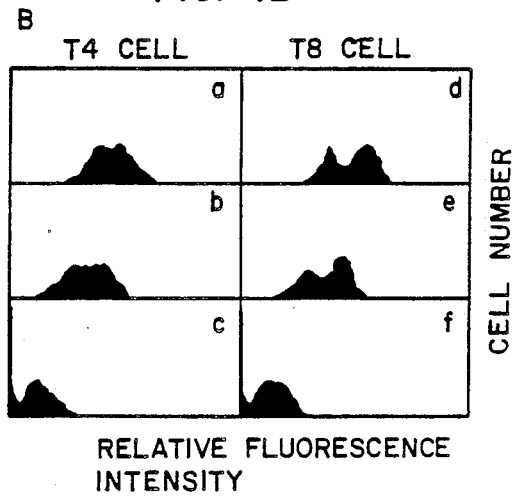

Referring to FIGS. 1A and 1B, data is provided to confirm the reactivity of the S6F1 monoclonal antibody with certain T lymphocytes. FIG. 1A represents a cytofluorographic analysis of unfractionated T lymphocytes, CD4+ lymphocytes and CD8+ lymphocytes derived from normal human blood from ten donors. $1 \times 10^6$ cells of each T lymphocyte population was analyzed for their reactivity with the S6F1 monoclonal antibody at a ratio of 1:1000 by indirect immunofluorescence on an EPICS®C flow cytometer commercially available from Coulter Corporation of Hialeah, Florida. The cell preparation and staining procedures employed were conventional and well known in the art of cell sorting. Each histogram displays the number of cells along the ordinate or Y-axis versus fluorescence intensity along the abscissa or X-axis thereof.

In this representative study showing the fluorescence profile of the expression of the S6F1 antigen on the referenced T lymphocytes, the S6F1 antibody was reactive with 17% of unfractionated T cells, 14% CD4+ lymphocytes and 58% of CD8+ cells. Thus, the S6F1 antigen was expressed preferentially on the CD8+ population of lymphocytes. The S6F1 antibody reacted with greater than 70% of null cells, granulocytes and the T cell line HSB in this study. However, it reacted with only 10% of cells in population of macrophages, B cells, B cell lines, i.e., Raji, Ramos, Nalms-1, EB virus transformed cell lines, hematopoietic lines U-937, K-562, KG-1 or the T cell lines Molt 4, CEM and JM derived from other conducted testing.

FIG. 1B represents a study of the reactivity of CD4 and CD8 lymphocytes from normal donors with varied dilutions of the known monoclonal antibody 2F12 which recognizes the LFA-1 antigen. Analysis was by indirect immunofluorescence using an EPICS®C cell sorter. Each histogram displays cell numbers versus fluorescence intensity. In histograms a and d using anti-LFA-1 antibody at a dilution of 1:100, a cell reactivity of 98% resulted. In histograms b and e using the monoclonal antibody at a dilution of 1:1000, a cell reactivity of 98% resulted. In histograms c and f using the antibody at a dilution of 1:10000, a CD4 cell reactivity of 52% and a CD8 reactivity of 58% resulted. This analysis reflects the variation in staining patterns of both CD4 and CD8 lymphocyte populations with the monoclonal antibody 2F12 specific to the LFA-1 antigen whereas the S6F1 monoclonal antibody showed preferential binding to CD8+ lymphocytes.

Since the S6F1 antibody was seen to react with a sizeable population of CD8+ lymphocytes, the antibody was utilized to subdivide the CD8+ population of peripheral blood lymphocytes to assess the functional heterogeneity of these cells. A test protocol was implemented to study whether alloreactive cytotoxic T lymphocytes, either precursor or effector cells, could be separated from CD8+ suppressor cells with the S6F1 monoclonal antibody. To determine whether the precursor of alloantigen-specific cytotoxic T cells belonged either to the S6F1+ or S6F1−population of CD8+ cells, the specific cell mediated lympholysis (CML) by subsets of CD8+ cells was examined.

CD8+ cells were freshly isolated using known procedures and labelled with the S6F1 antibody and developed with fluorescein-conjugated F(ab')2 goat anti-mouse F(ab')2 (Tago). The labelled CD8 cells were sorted using the EPICS®C cell sorter into CD8+S6F1+ and CD8+S6F1−populations as described in Morimoto et al., J. Immunol 134:1508-1515 (1985). Then, $1 \times 10^6$/ml of CD4+ cells obtained by complement-mediated lysis added to generate killer inducer function in this system were cultured with $1 \times 10^6$/ml of unfractionated CD8+ cells, sorted CD8+S6F1+ or CD8+S6F1−cells in the presence of equal numbers of irradiated allogenic stimulator cells, i.e., E-cells in multiple well culture plates in 5% $CO_2$ humidified at 37° C. After six (6) days of culture, CD4 cells were removed from culture by complement-mediated lysis of CD4+ cells. $^{51}Cr$ labelled release cell mediated lympholysis by subsets of CD8 cells was assayed after a four (4) hour cell incubation as described in Meuer et al., Proc. Natl. Acad. Sci, U.S.A. 79:4395-4399 (1982).

Figure 2A:
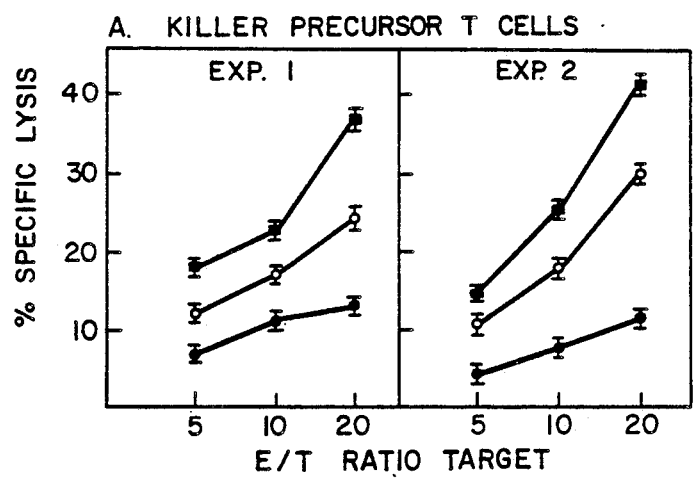
FIGS. 2A and 2B are graphs developed to identify the lymphocyte sub-population into which the cytotoxic effector cell is classified CD8 control cells are designated by a line drawn between open circles, CD8+S6F1− subset cells are designated by a line drawn between closed squares and CD8+S6F1+ subset cells are designated by a line drawn between closed circles.

Referring to FIG. 2A, the graph details % Specific Lysis along the ordinate and E/T Ratio Target along the abscissa. A pair of experimental tests were conducted as depicted in FIG. 2A. It appeared that the majority of cytoxic T cells against specific target cells resided in the CD8+S6F1−subset, while a small portion was found in the CD8+S6F1+ subset.

Figure 2B:
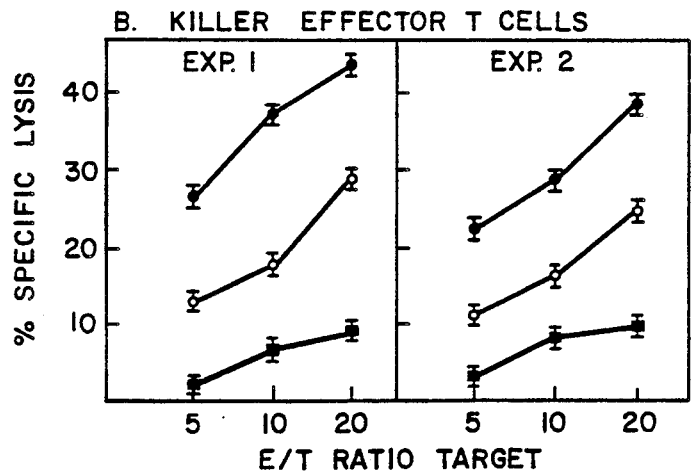

Referring to FIG. 2B, the data displayed establishes that the cytotoxic effector T cells belong to mixed lymphocyte reaction (MLR) activated CD8+S6F1+ cells and not CD8+S6F1−cells. The protocol followed to achieve this determination was as follows: $1 \times 10^6$ ml unfractionated T cells were sensitized with equal numbers of irradiated (5000 Rad) allogenic (E-) stimulator cells in final RPMI 1640 medium (10% pooled human AB serum-Pel Freeze), 4 mML-glutamine, 25 mM Hepes buffer (Microbiological Associates), 0.5% sodium bicarbonate and 10% penicillin-streptomycin in a 25 cm² flask in 5% $CO_2$ humidified atmosphere at 37° C. for six (6) days. Unfractionated T cells thus sensitized with allogenic E-cells were separated into CD8+S6F1+ and CD8+S6F1−subsets of cells by means of an EPICS®C cell sorter. Both unfractionated and fractionated CD8+ cells were analyzed in cell mediated lympholysis against $^{51}Cr$ labelled target cells comprising thawed cryopreserved allogenic (E-) cells cultured over an approximate 10-12 hour period and incubated for one (1) hour at 37° C. in a 0.2 ml of sodium chromate in saline solution (1 mCi/ml, New England Nuclear). The target cells, i.e., $^{51}Cr$ labelled cells, were washed and resuspended at $10^5$/ml in final media. A standard four (4) cytotoxity assay was performed using V-bottom wells of a culture plate. A pair of experiments was conducted as depicted in FIG. 2B.

In contrast to the data displayed in FIG. 2A, the CD8+S6F1+ lymphocyte population demonstrated greater allospecific killer effector activity than did the unfractionated CD8+ population. Virtually no killer effector activity was observed in the CD8+S6F1− lymphocyte population. Other data observed from these experiments, but not included herein, showed that the S6F1 monoclonal antibody did not block the effector function although the anti-MHC class I and anti-LFA-1 monoclonal antibodies blocked the killer effector function as described in Meuer et al., supra; Sanchez-Madrid et al., J. Exp. Med. 158:1785-1803 (1983); Sanchez-Madrid et al., Proc. Natl. Acad. Sci. U.S.A., 79:7489-7493 (1982). This data shows that killer precursor T cells are found in the CD8+S6F1− subset of cells, but the killer effector activity belongs to the CD8+S6F1+ subset.

The data developed by these tests suggest that the S6F1 antigen may become expressed on a S6F1 negative CD8+ cell population during a primary MLR reaction. A primary MLR was initiated using CD8+S6F1− lymphocytes combined with CD4+ cells and the T lymphocytes evaluated for expression of the S6F1 antigen. Three (3) separate experiments were conducted in which data developed showed 45-55% of CD8+S6F1− cells expressed the S6F1 antigen on their cell surfaces after MLR activation. These results indicate that the S6F1 antigen expression is induced on a S6F1 negative population of CD8+ cells.

Data was developed to determine which subset of CD8+ cells was activated to become suppressor effector cells as shown in FIG. 3A. Freshly isolated unfractionated T cells were separated into CD8+S6F1+ and CD8+S6F1− subsets using previously discussed technology and an EPICS®C cell sorter. Varying numbers of CD8 cells were added to $5 \times 10^4$ B cells and $2 \times 10^4$ CD4+ cells stimulated with pokeweed mitogen (PWM) in round bottom, multiple well, micro-culture plates and total IgG immunoglobulin production was measured after seven (7) days in culture. Culture supernatants for IgG secretion were determined by radio-immunoassay as described in Meuer et al., supra.

As shown in FIG. 3A, the addition of increasing numbers of unfractionated CD8+ cells resulted in the suppression of PWM driven IgG secretion by B cells in a dose dependent fashion. When increasing numbers of CD8+S6F1− cells were added to CD4+ and B cells, an even greater degree of suppression of IgG secretion was observed. In contrast, the addition of CD8+S6F1+ cells to the mixture of B and CD4+ cells resulted in only a slight decrease in IgG secretion. These results show that the precursor of CD8 suppressor cells belonged to the CD8+S6F1− subset of cells.

Data was developed to determine whether T cell suppressor activity was found in the CD8+S6F1+ population by examining the suppressor function of the subsets of CD8+ cells after MLR activation in an alloantigen-stimulated IgG synthesis system. Prepared T cells were activated in MLR against alloantigen for six (6) days and alloactivated T cells were separated into CD8+S6F1+ and CD8+S6F1− cells on an EPICS®C cell sorter. Unseparated CD8 and subsets of CD8+ cells were added to autologous peripheral blood lymphocytes (PBL) in the presence of irradiated alloantigen used MLR and the effects of alloantigen driven IgG synthesis was calculated as follows:

$$\% \text{ suppression} = 1 - \frac{\text{observed IgG}}{\text{IgG in no regulator cells}} \times 100$$

As shown in FIG. 3B, alloactivated unfractionated CD8+ cells suppressed alloantigen driven IgG synthesis in a dose dependent manner. The CD8+S6F1− population activated with alloantigen showed greater suppressor activity in this system than did the unfractionated CD8+ cells. However, alloantigen activated CD8+S6F1+ lymphocytes exhibited a minimal suppressor activity only when very large numbers of cells were added to these cultures. These results indicate that both suppressor precursor and suppressor effector cells belong to the CD8+S6F1− lymphocyte population. More importantly, the above results imply that suppression is probably not merely a manifestation of cytotoxicity.

In view of the efficacy of the S6F1 antigen in the identification of cytotoxic effector T cells, the structure of the antigen was analysed by immunoprecipitation procedures of the S6F1 and LFA-1 antigen using anti-2F12. The analysis data is presented in FIGS. 4A, 4B and 4C.

Cells from T cell-enriched cells (95% E+ cells) were activated with Concanavalin A (ConA) (20 μg/ml) for three (3) days and labeled with $^{125}$I by lactoperoxidase-catalysed iodination [per Hubbard et al., Biochemical Analysis of Membrane) (ed. Maddy, AH) P-427–501 (Chapman and Hall, 1976)], washed and then solubilized in lysis buffer (1% W/V Nonidet P-40 in 20 mM Tris-HCl buffer pH 8.0 containing 150 mM NaCl, 1 mM EDTA and 1 mM phenylmethyl (sulphony) fluoride). The lysates ($5 \times 10^7$ cell equivalents) were then incubated overnight at 4° C. with 5 microliters of ascitic fluid of the individual antibodies before precipitating with 50 microliters of 10% w/v Protein A: Sepharose. The immunoprecipitates were then washed once in lysis buffer with 0.1% (w/v) SDS and twice with lysis buffer alone, prior to analysis by SDS-PAGE as described in Laemmli, Nature (London) 227:680–684 (1970). Lysates from labeled peripheral blood lymphocytes were precleared with the TS1/18 antibody for four immunoprecipitations prior to precipitation with the S6F1 antibody. Lysates were labelled and prepared as described, after which the immune complexes were eluted from the beads by incubation in isoelectric focusing sample buffer (9.2M urea, 2% Nonidet P-40, 2% ampholines pH range 2-11 (Serva) at 50° C. for 30 min. Two dimension NEGPHE/SDS-PAGE analysis was done as previously described in O'Farrell, et al., Cell 12:1133–1142 (1977); Rudd et al., J. Biol. Chem. 200:1927–1936 (1985).

Figure 4A:
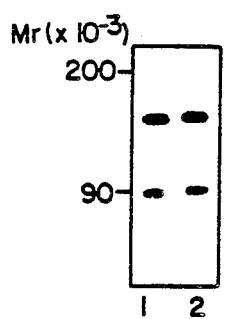
FIGS. 4A, 4B and 4C depict graphs developed to show immunoprecipitation analysis data of the S6F1 and LFA-1 antigens.

The FIG. 4 data depicts a composite of patterns of polypeptides precipitated by the S6F1 monoclonal antibody and the 2F12 monoclonal antibody which recognizes the LFA-1 antigen from Con A activated T cells. FIG. 4A displays two columns or lanes 1 and 2 in which the data of lane 1 relates to the S6F1 and lane 2 relates to the 2F12 monoclonal antibodies, respectively. Lane 1 shows that the S6F1 antibody precipitated two major bands at 180,000 daltons (Mr) and 95,000 daltons (Mr). Lane 2 shows that the 2F12 antibody precipitated a band pattern which appears to correspond to the alpha and beta subunits of the LFA-1 antigen, respectively.

Figure 4B:
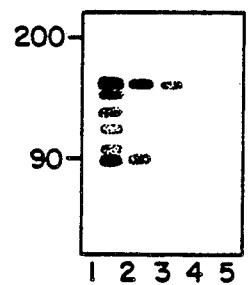

The data of FIG. 4B is derived from a direct demonstration of the identity of the S6F1 antigen made by sequential immuno-depletion and two dimensional non-equilibrium gel analyses (NEPHGE/SDS-PAGE). Lane 1 relates to the S6F1 antibody and lane 2 relates to the 2F12 antibody. The data of FIG. 4B shows that the 2F12 antibody to LFA-1 antigen completely deleted material with which the S6F1 reacted. It is noted that the monoclonal antibody TS1/18 had been shown to react with the beta subunit of the LFA-1 antigen. See Sanchez-Madrid et al., supra, both citations.

Figure 4C:
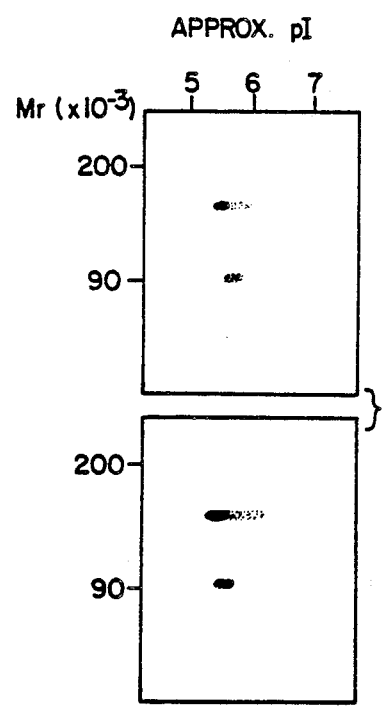

FIG. 4C presents data developed from analysis by 2-D NEPHGE/SDS-PAGE of the S6F1 and LFA-1 antibodies. This data shows that antibodies against the S6F1 and LFA-1 antigens precipitated two polypeptides at 180,000 daltons and 95,000 daltons which focused at an approximate isoelectric position of pH 5.3 and 5.7, respectively. The data of FIG. 4C supports the observation that the S6F1 monoclonal antibody binds the LFA-1 antigen.

Although the S6F1 and 2F12 monoclonal antibodies immunoprecipitate the same structure, their reactivity with functionally distinct cell subsets appears to differ. The data graphically displayed in FIGS. 1A and 1B showed that the S6F1 monoclonal antibody stained CD8+ lymphocytes preferentially whereas the 2F12 antibody exhibited a reactivity with CD4+ lymphocytes also. It is believed that the reactivity of CD8+ lymphocytes with the S6F1 antibody does not reflect simply a low affinity of the antibody for the LFA-1 antigen structure itself.

We determined from analyses conducted with the S6F1 monoclonal antibody that the actual epitope it recognizes appears not to be involved in the process of cytotoxicity because the antibody was unable to block this function. However, other known monoclonal antibodies directed against the LFA-1 antigen were able to effectively block this cytotoxicity process. See Sanchez-Madrid et al., supra. Further, the S6F1 antigen was determined to be expressed primarily on CD8+ cells, null cells and a small fraction of macrophages and B cells. The data developed does indicate that the epitope on the LFA-1 antigen recognized by the S6F1 antibody may be formed distantly on the molecule by the development of a binding site on the LFA-1 antigen involved in the adherence function to target cells.

Thus, the S6F1 monoclonal antibody can distinguish between cytotoxic effector and suppressor effector cells in CD8 lymphocyte populations by recognizing a novel epitope on the LFA-1 antigen. This unique characteristic of the S6F1 antibody is useful in diagnosing and defining the CD8 cytotoxic effector cell and to distinghish it from the suppressor effector cell especially by flow cytometric techniques and by other known assay techniques as well. For instance, it is known that CD8 cytotoxic effector cells play a key role in human graft rejection, such as, in rejection of renal and other grafts. The S6F1 antibody to CD8+S6F1 cytotoxic effector cells could identify these effector cells selectively and thereby be useful to enable the functioning of the suppressor cell population to be of therapeutic value in reversing allograft rejection. Thus, the specificity of the S6F1 monoclonal antibody might be useful in the treatment of ongoing graft rejection.

This specificity of the S6F1 monoclonal antibody within the class of CD8 cells is particularly unique and useful in view of the heretofore unavailability of an antibody which could provide such a positive and more precise phenotypic means to distinguish suppressor effector from cytotoxic effector cells within the CD8 class of lymphocytes. Monoclonal antibodies to define the CD8 precursor of the cytotoxic cells in the human immune system is discussed in Clement et al., J. Immunol. 133:2461-2468 (1984) but without achieving the results achievable with the S6F1 monoclonal antibody embodying this invention.

DEPOSIT

A cell line which produces the S6F1 monoclonal antibody corresponding to this invention has been deposited in the American Type Culture Collection, Rockville, Md. 20852 on Oct. 30, 1987, prior to the filing of this application. The cell line was assigned ATCC Accession No. HB 9579.

The complete diagnostic and possible therapeutic applications of the monoclonal antibody of the invention have not been determined. The administration of an effective amount of the antibody, either alone or coupled to a radioisotope, drug or toxin may have therapeutic benefit in human organ transplant procedures consistent with the characteristics of the monoclonal antibody described herein.

We claim:

1. A hybrid cell line derived by hybridoma technique which produces a monoclonal antibody which binds specifically to an epitope identified as the S6F1 epitope on an antigen identified as the LFA-1 antigen and which enables the monoclonal antibody to distinguish between cytotoxic effector cells and suppressor effector cells in human CD8 lymphocyte populations.

2. The hybrid cell line as described in claim 1 wherein said cell line is produced from the spleen cells of mice which were immunized with an immortalized splenocyte population derived from Herpesvirus saimiri infected white lip tamarin.

3. The hybrid cell line as described in claim 2 which produces mouse IgG, isotype antibody to S6F1 epitope.

4. The hybrid cell line as described in claim 1 in which said monoclonal antibody producing cells are derived from the murine cells.

5. The hybrid cell line as described in claim 1 which was derived from a fusion with mouse myeloma cells.

6. A hybrid cell line produced by hybridoma technique which has the identifying characteristics of the cell line on deposit with the American Type Culture Collection, Rockville, Maryland, having A.T.C.C. Accession No. HB 9579.

7. A monoclonal antibody which specifically binds to an antigen on the surface of a subset of T lymphocyte population, said antigen:
   (a) being detectible on CD8 cytotoxic effector cells and essentially undetectible on CD8 suppressor effector cells; and
   (b) defining a cell surface structure comprised of a 180,000 dalton and a 95,000 dalton molecular weight glycoprotein.

8. The monoclonal antibody of claim 7 in which said monoclonal antibody binds an epitope on the LFA-1 antigen.

9. The monoclonal antibody of claim 7 having mouse isotype IgG/which is produced by the cell line having the identifying characteristics of the sample on deposit with the American Type Culture Collection, A.T.C.C. No. HB 9579.

10. A monoclonal antibody which binds specfically to an epitope on the LFA-1 antigen of T lymphocytes in human peripheral blood and which binds preferentially to CD8 cytotoxic effector cells present in a population of CD8 cytotoxic effector and CD8 suppressor effector cells in peripheral blood lymphocytes.

11. The monoclonal antibody of claim 10 which binds the SF61 epitope.

12. A method of distinguishing between cytotoxic effector cells and suppressor effector cells in a sample of human CD8 lymphocyte populations comprising, contacting said sample with a monoclonal antibody identified as the S6F1 monoclonal antibody for a time and under conditions sufficient for the formation of immunological complexes between said S6F1 monoclonal antibody and CD8 cytotoxic effector cells and then detecting the immunological complexes resulting from said contact between said monoclonal antibody and cells in said sample, the cells complexed with said monoclonal antibody being CD8 cytotoxic effector cells.

13. The method of claim 12 including the step of labelling said monoclonal antibody with a detectible compound prior to contacting said sample with said monoclonal antibody such that said complexes are labelled with said detectible compound and said complexes, if any, are formed upon the contacting of said sample with said labelled monoclonal antibody.

14. The method of claim 12 including the step of separating the detected immunological complexes by cell sorting flow cytometric procedures.

15. The method of claim 13 in which said detectible compound is a fluorescent compound.

16. The method of claim 13 in which said detectible compound is an enzyme.

17. A murine monoclonal antibody of the mouse IgG$_1$ isotype which is specific for an epitope identified as the S6F1 epitope present on the surface of CD8 cytotoxic effector cells in peripheral blood lymphocytes.

18. The monoclonal antibody of claim 17 in detectibly labelled form.

19. The monoclonal antibody of claim 18 wherein said label is selected from the group consisting of a dye, a fluorescent compound, a radioactive element and an electron dense element.

20. The monoclonal antibody of claim 17 in which said monoclonal antibody is coupled to any one of the group consisting of a human therapeutic radioisotope, pharmaceutical and chemotoxin.

21. A method of detecting and measuring, in liquid biological sample, the S6F1 antigen on the surface of CD8 cytotoxic lymphocytes within the CD8 class of lymphocytes comprising contacting said sample with S6F1 antibody conjugated to a detectable label selected from the group consisting of a fluorescent compound, a radioactive element and an enzyme; allowing said conjugated, antibody to bind to said surface antigen; and then detecting and measuring the bound conjugated antibody.

22. The method of claim 21 including the step of flow cytometric cell sorting of the CD8 cytotoxic effector lymphocytes bound by said conjugated monoclonal antibody.

* * * * *

UNITED STATES PATENT AND TRADEMARK OFFICE
CERTIFICATE OF CORRECTION

PATENT NO. : 5,002,869

DATED : March 26, 1991

INVENTOR(S) : Stuart F. Schlossman and Chikao Morimoto

It is certified that error appears in the above-identified patent and that said Letters Patent is hereby corrected as shown below:

```
Column 2, line 4, change "(T8+ -)" to --(T8+Mo1-)--

Column 5, line 44, change "cytoxic" to --cytotoxic--.

Column 7, line 3, change "was calculated as follows:"
          to --were assessed.  Percent suppression of
          IgG synthesis was calculated as follows:--.
```

Signed and Sealed this

Twenty-ninth Day of September, 1992

Attest:

DOUGLAS B. COMER

*Attesting Officer*      *Acting Commissioner of Patents and Trademarks*